United States Patent [19]

Romaine

[11] Patent Number: 5,380,337
[45] Date of Patent: Jan. 10, 1995

[54] MESH-TYPE SKIN BIOPSY APPLIANCE

[76] Inventor: Richard A. Romaine, 475 SW. View Crest Dr., Gresham, Oreg. 97080

[21] Appl. No.: 185,526

[22] Filed: Jan. 24, 1994

[51] Int. Cl.⁶ .............................................. A61B 17/00
[52] U.S. Cl. .................................. 606/131; 128/749; 604/115; 604/116
[58] Field of Search ............... 128/743, 749, 751, 753, 128/754, 757, 846, 888; 606/131; 602/47, 59; 604/307, 131, 115, 116

[56] References Cited

U.S. PATENT DOCUMENTS

| | | | |
|---|---|---|---|
| 2,390,184 | 12/1945 | Jeng | 602/59 X |
| 2,522,309 | 9/1950 | Simon | 128/743 |
| 3,073,303 | 1/1963 | Schaar | 602/59 |
| 3,289,670 | 12/1966 | Krug et al. | 128/743 |
| 3,307,545 | 3/1967 | Surowitz | 602/47 |
| 4,702,237 | 10/1987 | Gianopolous et al. | 602/59 X |
| 5,104,620 | 4/1992 | Wiley et al. | 128/743 X |
| 5,123,907 | 7/1992 | Romaine | 604/195 X |
| 5,144,958 | 9/1992 | Krueger et al. | 128/888 X |
| 5,981,142 | 1/1991 | Dachman | 128/749 |

FOREIGN PATENT DOCUMENTS 1104098  11/1955  France ................. 128/888

*Primary Examiner*—Sam Rimell
*Attorney, Agent, or Firm*—Eugene D. Farley

[57] ABSTRACT

A mesh appliance and method for use in excising skin samples from stretched skin, as in taking punch biopsies. The appliance is placed on a stretched skin area and maintains the skin in stretched condition during the sample incising operation. It is used with the skin stretched in the direction perpendicular to the skin Langer's lines, thereby producing a skin opening which is elliptical in contour and effectively sutured.

6 Claims, 1 Drawing Sheet

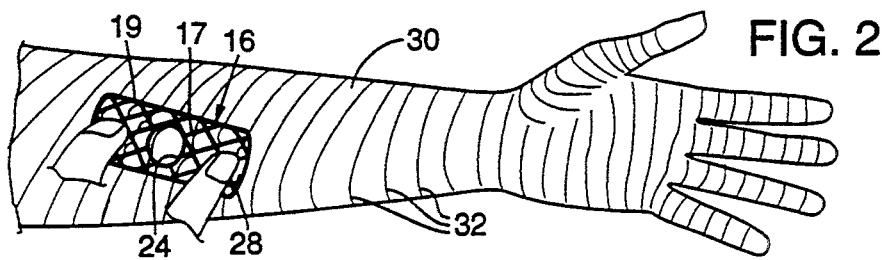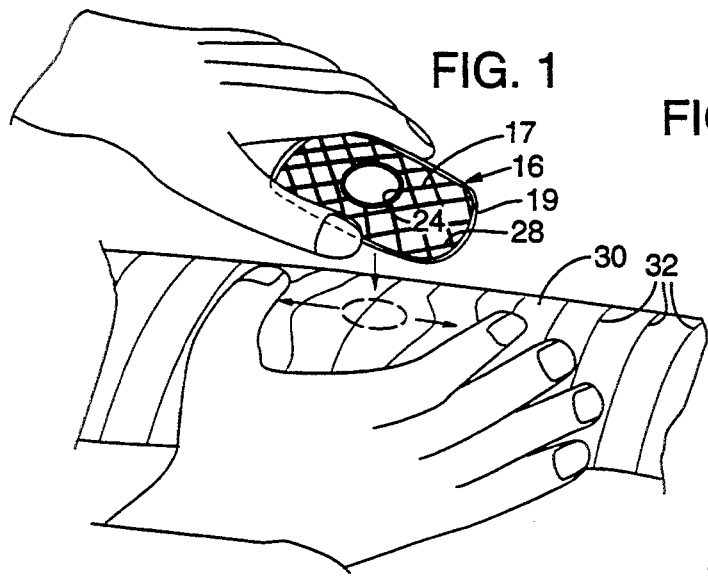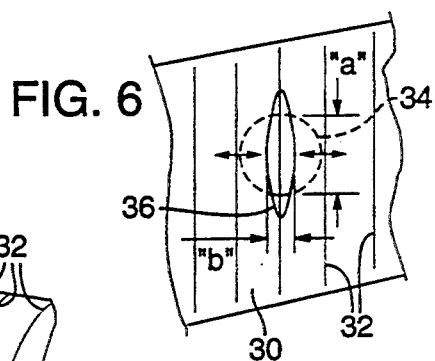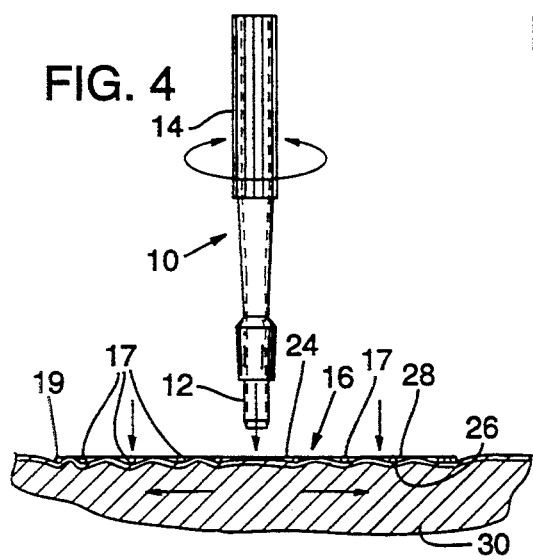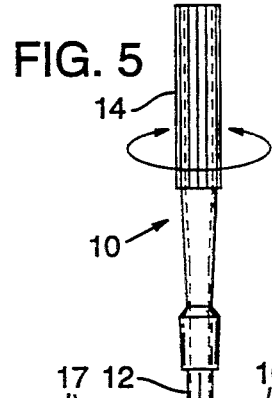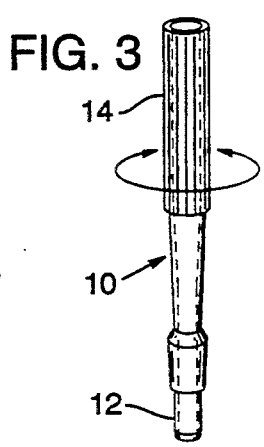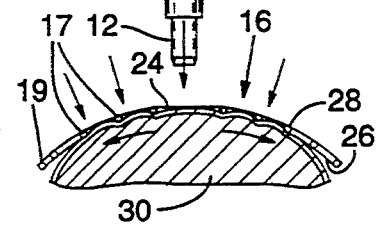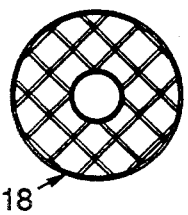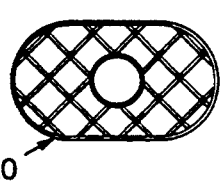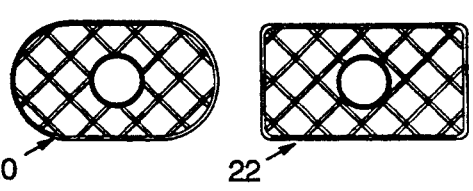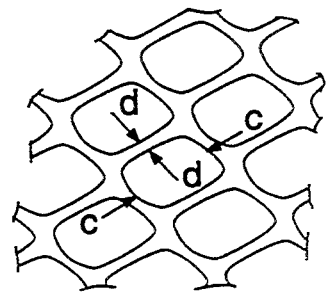

MESH-TYPE SKIN BIOPSY APPLIANCE

BACKGROUND OF THE INVENTION

1. Field of the Invention

This invention relates to an appliance for use in excising skin samples from stretched skin, e.g. to a skin biopsy appliance.

2. Description of Prior Art

It frequently is necessary in the practice of medicine to excise a skin sample from a given skin area. An example of such a procedure is the excising of skin samples in the performance of biopsies.

As is well known, a biopsy is a surgical procedure performed on the skin or other organ to sample tissue structure and cell content, usually to assist in disease diagnosis.

A skin biopsy may be accomplished in different ways. For instance, a scalpel blade may be used to cut into the skin and excise samples of various sizes. This procedure almost always requires suturing the wound edges together.

In the alternative, the biopsy sample may be obtained by slicing or shaving the skin horizontally to remove an elevated portion. This procedure usually does not require suturing.

The method of sampling skin tissue most often used by dermatologists relies upon the use of an instrument called a skin punch. This is a short, pencil-shaped tool having one end in the form of an open cylinder provided with a sharp, cutting blade. The punch is held at its upper, solid end by the thumb and one or two fingers and twirled while it rests on and is pressed lightly into the skin surface. This creates a plug of tissue which can be snipped loose from its underlying attachment and submitted to the laboratory for examination.

The punch biopsy routine may or may not require suturing. If the defect is only 1–3 mm in diameter, natural and unassisted healing usually will be adequate. However, if the defect is larger, suturing will hasten the healing. It also will result in the formation of a less conspicuous scar.

Although widely used, the foregoing procedure has a significant disadvantage. The biopsy punch inherently cuts a circular opening in the skin. When the edges of a circular opening are brought together, the distal portions splay out and pucker to form nipple-like protrusions. The resulting scar is unsightly and cosmetically undesirable.

To overcome this problem, a procedure has been developed which takes advantage of the fact that there exist in the skin variously disposed lines of natural skin tension. These are called "Langer's lines". They may be taken advantage of to create in the skin an elliptical opening rather than a circular one. The elliptical opening is readily amenable to effective suturing procedures.

Accordingly, to carry out the skin sampling procedure a lateral stretching force is applied to the skin in the skin sampling area. This force is applied in the direction perpendicular to the lines of greater tension.

The stretched skin then is incised to make a substantially round cut defining the sample. The stretching force is removed and the sample excised by cutting or snipping it away from the anchoring tissue.

As this is done, the opening in the skin, which originally is circular, becomes elliptical. This is owing to deformation by the lines of tension (Langer's lines) which exist in the skin. As noted, the elliptical opening may be sutured effectively.

However, even this improved technique is characterized by a problem the solution to which is the object of the present invention.

In carrying out a punch biopsy, the surgeon normally stretches the skin in the biopsy area by applying stretching force perpendicular to Langer's lines with the thumb and forefinger of one hand while manipulating the biopsy punch with the other hand. It is the surgeon's intention to maintain the stretching tension for the entire duration of the sampling procedure.

In practice, this may be difficult to do.

First, because of absorption in his work, distraction, fatigue, inattention, or other disturbing factors, the surgeon at the critical moment of taking the biopsy sample may relax the skin-stretching pressure, or his fingers may slip. As a result, the punched out opening ("defect") in the skin assumes a round configuration rather than the desired elliptical configuration.

Secondly, the surgeon for any of the above reasons may apply the stretching force in a direction other than the desired direction precisely perpendicular to the Langer's lines. In either case, the result is the same. The desired elliptical skin opening is not obtained.

An appliance and method for overcoming the foregoing problem is set forth in my U.S. Pat. No. 5,123,907. While the appliance and procedure described therein successfully overcome the problem, it remains to provide an appliance and method which give the surgeon a view of the skin area which underlies the appliance so that he can position the appliance accurately and study the unique disease characteristics of the underlying skin.

It also remains to provide a method and appliance which permits tissue exudate and serum to escape during the surgical procedure. Otherwise, an accumulation of this material lubricates the underside of the appliance and causes it to slip out of position.

Still further, it remains to provide a method and appliance which, independently of any applied adhesive material to the skin-contacting surfaces of the appliance, provides an anchoring function which anchors the appliance temporarily in place throughout the entire surgical procedure.

It is the general purpose of the present invention to provide such an appliance and method.

THE PRESENT INVENTION

In its broad aspects, the skin sample excising appliance of my invention comprises a mesh work piece sized to overlie the selected skin area and has a central opening dimensioned to clear the biopsy punch or other cutting instrument with which it is to be used. The material has a mesh size dimensioned to make visible to the operator the skin area involved and to allow passage of exudate, including blood and blood serum. It further has a mesh size which is predetermined to create friction by permitting the skin, which is under slight compression, to pop up through the mesh. This anchors the appliance temporarily to the skin surface and prevents it from slipping.

Accordingly, in use, lateral pressure is exerted perpendicular to the Langer's lines by the fingers of the hand which later will hold and use the punch. The appliance is placed between the pressing fingers which establish the intended ideal orientation and magnitude of pressure.

It then is held down and in place by the non-biopsying hand. This holds the underlying stretched skin in its desired optimal stretched condition while the skin sample is incised.

If the surgeon's fingers twist or relax, there will result no change in the surgery field, tension or orientation because the appliance will keep the skin stretched, as it was at the time of appliance placement. The desired easily and effectively-sutured elliptical opening in the skin accordingly is obtained.

THE DRAWINGS

In the drawings:

FIG. 1 is a top perspective view including a section of the ventral forearm with the Langer's lines illustrated thereon, depicting the manner of placement of the herein described appliance.

FIG. 2 is a top perspective view of the ventral forearm and palm illustrating the appliance placed thereon in position for incising the skin sample.

FIG. 3 is a top perspective view of a conventional skin biopsy punch of the class with which the herein described appliance may be used.

FIGS. 4 and 5 are views in elevation, partly in section, illustrating the manner of use of the appliance of my invention with the punch of FIG. 3.

FIG. 6 is a diagrammatic view illustrating the manner in which the punch-appliance combination produces an elliptical opening in the skin following the skin-sampling procedure;

FIGS. 7, 8 and 9 are schematic plan views illustrating various contours which may be assumed by the appliance.

FIG. 10 is a fragmentary plan view illustrating a typical mesh work piece which is used in the appliance of the invention.

DESCRIPTION OF PREFERRED EMBODIMENTS OF THE INVENTION

As indicated above, the herein described appliance for use in obtaining skin samples from stretched skin is adapted for use particularly with a biopsy punch such as is illustrated in FIG. 3.

The punch 10 comprises a cylindrical cutter 12 on the end of a shaft 14 which preferably has a knurled segment for positive gripping by the operator.

In use, the punch is placed against the tissue area to be sampled and twirled back and forth with the fingers as indicated in FIG. 3. As this is done, pressure transmitted to the cutting edge of the punch carries it downwardly, incising the tissue to the desired depth and producing a cut defining the sample. The punch then is withdrawn. Upon withdrawal of the punch, the sample is excised with a scissors or other suitable cutting tool.

The appliance of my invention is used in combination with a punch of the character described. It is indicated generally at 16. It comprises a piece of size and contour appropriate for its intended application. Its contour may be round, elliptical, or rectangular, as shown in the embodiments indicated at 18, 20 and 22, respectively, of FIGS. 7, 8 and 9. Whatever its shape, the appliance comprises a piece or plate 17 of stiff mesh work enclosed by a frame 19. It may be made integrally from a single piece of suitable structural material, such as stiff but pliant plastic or metal. Whatever its composition, it should be heat and corrosion resistant so that it can be sterilized.

Mesh work 17 has mesh dimensions predetermined to achieve the objectives of the invention namely (1) To make visible to the operator the selected operatives site.
(2) To allow the passage of exudate, including blood and blood serum.
(3) To create frictional engagement of the appliance with the underlying skin by permitting the skin, compressed slightly by the pressure of application, to pop up through the mesh openings. This anchors the appliance temporarily in place so that it will not slip.

To achieve these objectives the mesh openings c—c of FIG. 10 should be from 5 to 10 mm in diameter. The filament thickness d—d of FIG. 10 should be from ½ to 1½ mm. If the filaments are too thick, slipping of the appliance during use is promoted. If they are too thin, they may cut into the flesh. However, even a very fine filament usually will not cut, when taken together with its many neighboring filaments. A single spike of a bed of spikes does not penetrate.

For effective contact, the mesh either is sufficiently flexible to conform to the underlying contour, or is made in a slightly concave configuration.

The appliance has a central hole 24 sized to receive punch 10. It has an undersurface 26 and an upper surface 28. Both surfaces are skid resistant: the undersurface in order to maintain the appliance properly in position during the excising operation, and the upper surface to insure that the surgeon's fingers will not slip.

The manner of using the appliance in conjunction with the biopsy punch is illustrated particularly in FIGS. 1 and 2.

In the illustrated situation, the sample to be taken is a sample of skin from the ventral forearm 30. As illustrated schematically in the drawings, and as discussed hereinabove, the skin in this area of the body is characterized by the presence of Langer's lines or tension lines 32. These circle the arm roughly parallel to each other in the indicated manner.

In carrying out the procedure, the surgeon first with one hand stretches the skin in a direction perpendicular to the Langer's lines. As illustrated in FIG. 1 the stretching is accomplished by exerting lateral pressure using the fingers of the hand which later will hold and use the biopsy punch.

The appliance is placed between these laterally pressing fingers. It then is held down and in place in its ideal orientation using the correct amount of pressure by the fingers of the non-biopsying hand. It now holds the underlying skin in the desired position and orientation, as illustrated in FIG. 2.

While holding the appliance in position with one hand, the surgeon grasps the biopsy punch with his operating hand; locates it centrally of opening 24 in the appliance; and with the twirling motion illustrated in FIGS. 4 and 5 incises the skin. During this operation he maintains digital pressure on the upper surface 28 of the appliance. This prevents his fingers from slipping. It also causes the slightly compressed skin of both patient and surgeon to project into the mesh openings, preventing the appliance from slipping, FIGS. 4 and 5. This condition obtains even if the surgeon's stabilizing fingers inadvertently should twist or relax pressure. In that event, there will be no change in the surgery field tension or orientation because the appliance by friction will keep the skin stretched as it was at the time of appliance placement.

In this manner it is insured that the stretching pressure will be exerted continuously in the direction normal to the Langer's lines so that the desired result illustrated in FIG. 6 is obtained. As shown in that figure, the punch cuts a circular opening 34 indicated in dashed lines and having a dimension "a". However, because of the tension forces present in the skin, upon removal of the punch and skin sample and release of the lateral pressure on the skin, the opening in the skin assumes the elliptical shape 36. This has the dimension "b", ideal for suturing.

Having thus described in detail a preferred embodiment of the present invention, it will be apparent to those skilled in the art that many physical changes may be made in the apparatus without altering the inventive concepts and principles embodied therein. The present embodiment is therefore to be considered in all respects as illustrative and not restrictive, the scope of the invention being indicated by the appended claims.

I claim:

1. In combination with a biopsy punch, a stretched-skin-excising appliance comprising:
    a) a stiff piece of mesh material sized to overlie a selected skin area and having an opening dimensioned to clear the punch,
    b) the material having mesh dimensions predetermined to make visible to an operator the said selected skin area and to allow passage of exudate, including blood and blood serum,
    c) the material having a skid-resistant, skin-contacting surface and an opposite pressure-applying surface.

2. The combination of claim 1 wherein the meshes of the mesh material have a mesh size predetermined to create friction by permitting compressed skin to pop up through the meshes, thereby releasably anchoring the appliance to the skin.

3. The combination of claim 2 wherein the meshes have a mesh opening size of from 5 to 10 mm and the plate is composed of filaments having a thickness of from ½ to 1½ mm.

4. The combination of claim 2 wherein the piece of mesh material is fabricated from stiff plastic material or metal.

5. The combination of claim 2 wherein the piece of mesh material is stiffly flexible, to conform to the skin contour during use.

6. The method of excising skin samples from skin having Langer's lines, which comprises:
    a) stretching the skin in a sample area in a direction substantial perpendicular to the direction of the skin Langer's lines,
    b) providing an appliance comprising a meshwork plate having an opening dimensioned to clear a skin incising tool,
    c) the appliance having a skin-contacting surface and an opposite pressure-applying surface,
    d) placing the appliance on the stretched skin with the skin-contacting surface in pressure contact with the skin and the pressure-applying surface positioned for the application of external pressure in amount sufficient to maintain the skin beneath the appliance in stretched condition during the sample incising operation, and in amount sufficient to cause the compressed skin to pop up through the meshes, temporarily anchoring the appliance in position,
    e) incising the stretched skin to make a substantially round cut defining the sample,
    f) excising the sample, and
    g) removing the appliance from the stretched skin area, thereby permitting the tension forces of the skin to alter the round configuration of the hole to an elongated, substantially elliptical configuration.

* * * * *